(12) United States Patent
Thomas et al.

(10) Patent No.: US 8,440,084 B2
(45) Date of Patent: May 14, 2013

(54) WASHABLE ANAEROBIC DIGESTER WITH FIXED BIOFILM

(75) Inventors: Morgan Jean-David Michael Thomas, Sart Messire Guillaume (BE); Jacques Benoit Michotte, Wavre (BE)

(73) Assignee: Greenwatt, Tourinnes-Saint-Lambert (BE)

( * ) Notice: Subject to any disclaimer, the term of this patent is extended or adjusted under 35 U.S.C. 154(b) by 524 days.

(21) Appl. No.: 12/682,119

(22) PCT Filed: Oct. 8, 2008

(86) PCT No.: PCT/EP2008/063440
§ 371 (c)(1),
(2), (4) Date: Aug. 2, 2010

(87) PCT Pub. No.: WO2009/047259
PCT Pub. Date: Apr. 16, 2009

(65) Prior Publication Data
US 2010/0307970 A1   Dec. 9, 2010

(30) Foreign Application Priority Data
Oct. 8, 2007   (EP) .................................. 07118022

(51) Int. Cl.
*C02F 3/28* (2006.01)
*C12M 1/113* (2006.01)

(52) U.S. Cl.
USPC ............ 210/603; 210/615; 210/175; 210/194

(58) Field of Classification Search .................. 210/603, 210/615, 616, 617, 618, 150, 151, 175, 277
See application file for complete search history.

(56) References Cited

U.S. PATENT DOCUMENTS

| | | | | |
|---|---|---|---|---|
| 4,179,374 A | * | 12/1979 | Savage et al. | 210/151 |
| 4,725,357 A | * | 2/1988 | Downing et al. | 210/611 |
| 5,653,883 A | | 8/1997 | Newman et al. | |
| 6,551,510 B1 | * | 4/2003 | Bakke et al. | 210/603 |

FOREIGN PATENT DOCUMENTS

| | | |
|---|---|---|
| EP | 0 265 303 | 4/1988 |
| EP | 0 504 065 | 9/1992 |
| WO | WO 91/19682 | 12/1991 |

OTHER PUBLICATIONS

International Search Report dated Feb. 25, 2009 and issued to international application No. PCT/EP2008/063440.

* cited by examiner

*Primary Examiner* — Fred Prince
(74) *Attorney, Agent, or Firm* — Knobbe, Martens, Olson & Bear LLP

(57) ABSTRACT

An effluent treatment apparatus which is a flushed anaerobic digester with fixed biofilm (FAD system) is disclosed. The FAD system creates and maintains an optimum environment for the development and activity of anaerobic bacteria. The FAD system can be used for all treatment methods for anaerobic bacteria, regardless of function. The FAD system is intended for the production of biogas.

20 Claims, 2 Drawing Sheets

US 8,440,084 B2

WASHABLE ANAEROBIC DIGESTER WITH FIXED BIOFILM

CROSS-REFERENCE TO RELATED APPLICATIONS

This application is the U.S. National Phase under 35 U.S.C. §371 of International Application PCT/EP2008/063440, filed Oct. 8, 2008, which was published in a non-English language, which claims priority to EP 07118022.8, filed Oct. 8, 2007.

SUMMARY

This invention relates to an effluent treatment apparatus, and in particular relates to a washable anaerobic digester with fixed biofilm. The invention also relates to a process of washing an effluent treatment apparatus. This invention relates to a process for effluent treatment using an apparatus according to the invention.

STATE OF THE ART

Anaerobic digestion is a process known for many years, and the use of a support (fixed or mobile) for the attachment of bacteria is used in several types of digesters. The digester with fluid recirculation, with upward or downward flow, allows homogenizing the liquid contained in the reactor. The important parameters to control this type of process are temperature, hydraulic residence time of the liquid to be treated, the recirculation speed and pH. In the precise case of biogas production, the temperature is around 37° C. for mesophile and 55° C. for thermophilic bacteria. Hydraulic residence time varies between 1 h and 50 h. The pH ranges between 6 and 8. The recirculation speed ranges between 1 and 20 mm/s. This low speed does not increase the biofilm detachment phenomenon.

The methods with support use the property of bacteria to clump together in the form of a biofilm and have the advantage of being more robust than the methods without support that use the property of bacteria to clump together to form flakes. Processes without support are more unstable and react to the slightest change of the environment: temperature, pH, recirculation speed. These processes require high-performance control systems to achieve good results. Processes with support more easily accept changes but offer less load capacity. In the precise case of biomethanation, processes without support can accept loads of up to 100 kg COD (chemical oxygen demand: the quantity of oxygen required to oxidize all of the organic matter, which represents the total amount of decomposable organic matter) per day and per $m^3$ of digester while processes with support are limited to 40 kg COD per day per $m^3$ of digester.

Processes with support all have the same problems of control of the thickness of the biofilm. Bacteria always tend to multiply, which increases the thickness of the biofilm. If this thickness is not properly controlled, it ends up being too large, which greatly reduces the accessibility of the substrate to lower layers of bacteria and leads to the clogging of the support.

Processes with support use materials with a large surface area available for attachment per $m^3$. This ratio varies depending on apparatuses from 100 to 800 $m^2/m^3$. However the correspondence between the number of $m^2/m^3$ and biogas production or digestion of substances by the bacteria is not proportional.

SUMMARY OF THE INVENTION

The invention relates to an apparatus for converting certain substances by putting them in contact with bacteria. The bacteria digest these substances to reject other substances. These bacteria are attached to a support in the form of a biofilm. More specifically this invention has been developed to transform organic waste in liquid form into biogas.

This invention relates to a washable anaerobic digester with fixed biofilm, also known as FAD system ("Flushed Anaerobic Digester with Fixed Biofilm") or effluent treatment apparatus.

The term "digester" as used in this invention relates to an apparatus that produces biogas through a fermentation process of organic matter. The "biogas" refers to a gas produced by fermentation of organic matter in the absence of oxygen. Biogas is composed primarily of methane ($CH_4$), for example between 50 and 80%, and carbon dioxide ($CO_2$), for example between 20 and 50%.

The term "biofilm" refers to a community of microorganisms—in this case bacteria—adhering to each other and to a surface.

In a first aspect, this invention relates to an effluent treatment apparatus (or washable anaerobic digester with fixed biofilm, or FAD system) comprising at least two tanks joined to each other at the top and/or at the bottom through one or more connections (connection lines) in which at least one of said tanks comprises:
  a gas storage area,
  an area of effluent treatment containing a fixed or mobile support for the attachment of bacteria,
  an area of effluent storage (wash water), and
  a settling area.

The apparatus according to the invention is characterized in that said gas storage area is located above the effluent treatment area. The apparatus according to the invention is characterized in that the effluent storage area is located above the effluent treatment area. The apparatus according to the invention is characterized in that said settling area is located below the treatment area.

In addition, the apparatus according to the invention is characterized in that a connection is provided between the gas storage areas of said tanks. The apparatus according to the invention is also characterized in that a connection is provided between the settling areas of said tanks.

In another embodiment of the invention, the apparatus is characterized in that it comprises an isolation valve located in the connection provided between the settling zones of said tanks.

The apparatus according to the invention is characterized in that it may comprise a control valve, which is preferably located in the connection provided between the settling zones of said tanks.

The effluent treatment apparatus also comprises a conduit or connection to supply effluent to the apparatus and a conduit or connection for the evacuation of the effluent, after treatment, from the apparatus, said conduits being functionally related to said tanks.

In another embodiment, the apparatus comprises a conduit or connection for the evacuation (settling) of sludge(s), said conduit being functionally connected to the bottom of said tanks. The effluent treatment apparatus also comprises a conduit or connection for the evacuation of gas, preferably biogas, from the apparatus, said conduit being functionally connected to at least one of said tanks, and preferably said conduit being functionally connected to the top of said tanks.

The apparatus according to the invention is characterized in that it may comprise a recirculation pump. The apparatus according to the invention is characterized in that it may comprise an evacuation pump. The apparatus according to the invention is characterized in that it may comprise at least one heat exchanger. Preferably, the recirculation pump and heat exchanger are provided on a conduit that is functionally connected to said tanks. In another embodiment, said evacuation pump is provided on the conduit for the evacuation of sludge.

The specificity of FAD system is to create and maintain an optimal environment for the development and activity of anaerobic bacteria. The FAD system is usable for all treatment methods using anaerobic bacteria regardless of their functions. The FAD system was developed for the production of biogas.

Many processes exist that use supports, fixed or mobile, for bacteria. Bacteria then clump in the form of a biofilm on the support. These processes have in common the problems of clogging of the supports and the accessibility of the substrate to the bacteria, by the uncontrolled growth of the biofilm. The FAD system gives the possibility to perfectly control the thickness of the biofilm.

The FAD system consists of at least two tanks that may be similar or not. These tanks are composed of several areas: a storage area for the gas produced by bacteria, an effluent storage area (wash water), an area containing the support for bacteria, and a settling area. The apparatus and process according to the invention use pumps, valves and heat exchangers if keeping it at a given temperature is necessary.

In another aspect, the invention relates to a process of washing of an effluent treatment apparatus according to the invention including the periodic creation of hydrodynamic constraints in the apparatus. The process comprises the following steps:

isolate the tanks from the bottom thereby achieving a volume of effluent in the effluent storage area of said apparatus, create a level difference in the effluent in said tanks, and release said volume of effluent in a few seconds.

The term "hydrodynamic constraints" as used in this application refers to the consideration of the internal forces that arise in a fluid when a certain speed or pressure is applied to it.

The term "isolate" the tanks from the bottom is used as a synonym for "close the connection between" the tanks from the bottom.

The term "effluent" is used to describe the liquid (for example water) loaded with biodegradable organic matter that can be processed in a digester. In the case of biomethanation, the effluent is mainly responsible for volatile fatty acid. It is the volatile fatty acids that are digested by bacteria to form biogas. When the volatile fatty acids present in the effluent are consumed, it is said that the effluent is purified.

The process is characterized in that the periodic creation of the hydrodynamic constraints is set by adjusting the operation of said isolation valve of the tanks, and/or said control valve, and/or recirculation pump.

More particularly, according to the invention, in an embodiment, hydrodynamic constraints are created, preferably in a periodic manner:

by operating an isolation valve of the tanks, said valve preferably being provided on the connection linking the tanks from the bottom, and/or by operating a control valve, said valve being preferably provided on the connection linking the tanks from the bottom, and/or by operating a recirculation pump, said pump being preferably provided on the connection linking the tanks from the top.

This invention therefore relates to a process of washing an effluent treatment apparatus according to the invention comprising the following steps:

obtain a volume of effluent in the effluent storage area of said apparatus by closing an isolation valve of the tanks, said valve being provided on the connection linking the tanks from the bottom to close the connection between said tanks from the bottom, get a level difference in the effluent in said tanks, preferably by activating a recirculation pump, recirculate the effluent by releasing, preferably in a few seconds, said volume of effluent, by opening the isolation valve of the tanks until obtaining an equilibrium level of effluent in said tanks.

The process is characterized in that the direction of recirculation of the effluent can be reversed. The term "recirculating" or "moving" means that the effluent flows in a loop between the two tanks, and its direction of rotation can be reversed.

The process is also characterized in that said washing process is repeated periodically. The term "periodically" in this context refers to a repetition of the process for example a number of times, for example ranging from once to several tens of times, during a few minutes, once per day or per week or per month.

As shown in FIG. 4, for example, the level of effluent in the effluent storage area can vary between a maximum (Hmax) and minimum (Hmin) level and $\Delta H$, corresponding to the difference between Hmin, and Hmax which is the maximum effluent level difference
that can be obtained in this process. The speed of the effluent in the tanks is determined by the difference in level between Hmax and Hmin and the passing section through the isolation valve and the opening speed of this valve.

In one embodiment, this mode of operation of the apparatus can periodically create strong hydrodynamic constraints and during the washing period a high fluid (effluent) speed, e.g. up to 0.25 m/s 1 m/s, 5 m/s or even 10 m/s. Therefore, in another embodiment, this invention relates to a process in which the recirculation speed of the effluent during the washing period is between 0.1 m/s and 10 m/s, for example between 0.25 m/s and 10 m/s, for example between 0.5 m/s and 7 m/s, or between 2.5 m/s and 5 m/s. For example strong hydrodynamic constraints are obtained when the process allows obtaining a variation (difference) in the maximum level of effluent ($\Delta H$) in the storage area. The speed during the washing period is typically a few millimeters per second.

The process according to the invention provides a recirculation flow, outside the washing period, of the effluent that is between half and twice the volume of the two tanks per hour.

In another embodiment, the washing process can be used to increase the activity of the biofilm. In this case the variation ($\Delta H$) in the level of the effluent is preferably not maximal. Level variations, which are smaller than the maximum difference ($\Delta H$), in this context show level variations resulting for example from the opening of the isolation valve, causing sufficient hydrodynamic constraints to increase the accessibility of the substrate (effluent) to bacteria of the lower layers of the biofilm, but not enough to detach the biofilm. This operating mode can also be applied periodically. The term "periodically" in this context refers to a repetition of the process for example every x minutes, x being between 0.1 and 60 minutes, for example between 1 and 30 minutes or between 5 and 45 minutes.

This invention also relates to the use of the effluent storage area as a reservoir for the washing of the biofilm on the support of the apparatus according to this invention.

The importance of the hydrodynamic constraints expected according to the invention in the process of digestion is very great because they allow for better homogeneity of the effluent to be treated and improved accessibility of the substrate (effluent) to bacteria. In this case in which an apparatus with support is used, they also allow controlling the thickness of the biofilm.

In another aspect, the invention relates to a process for effluent treatment, preferably to a process of treatment using anaerobic bacteria, and for example a process for transforming liquid organic waste into gas, preferably biogas (and therefore a process for the production of biogas), using an apparatus according to the invention.

The general principle is a low-energy means for washing a biofilm, i.e. detaching the unwanted portion of a biofilm by the use of two or more interconnected tanks 1, 2 in which progressively a level difference is created that will cause severe hydrodynamic constraints when opening the isolation valve 5 which allows for the equalization of levels.

Figures 1, 2, 3:
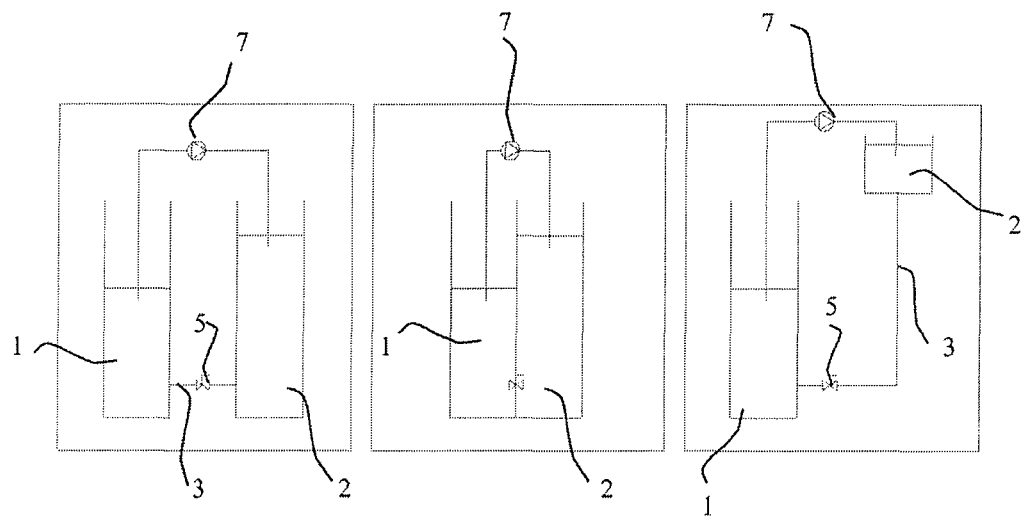
FIGS. 1, 2 and 3 are general representations of the various possible configurations (this is not exhaustive).
Figure 4:
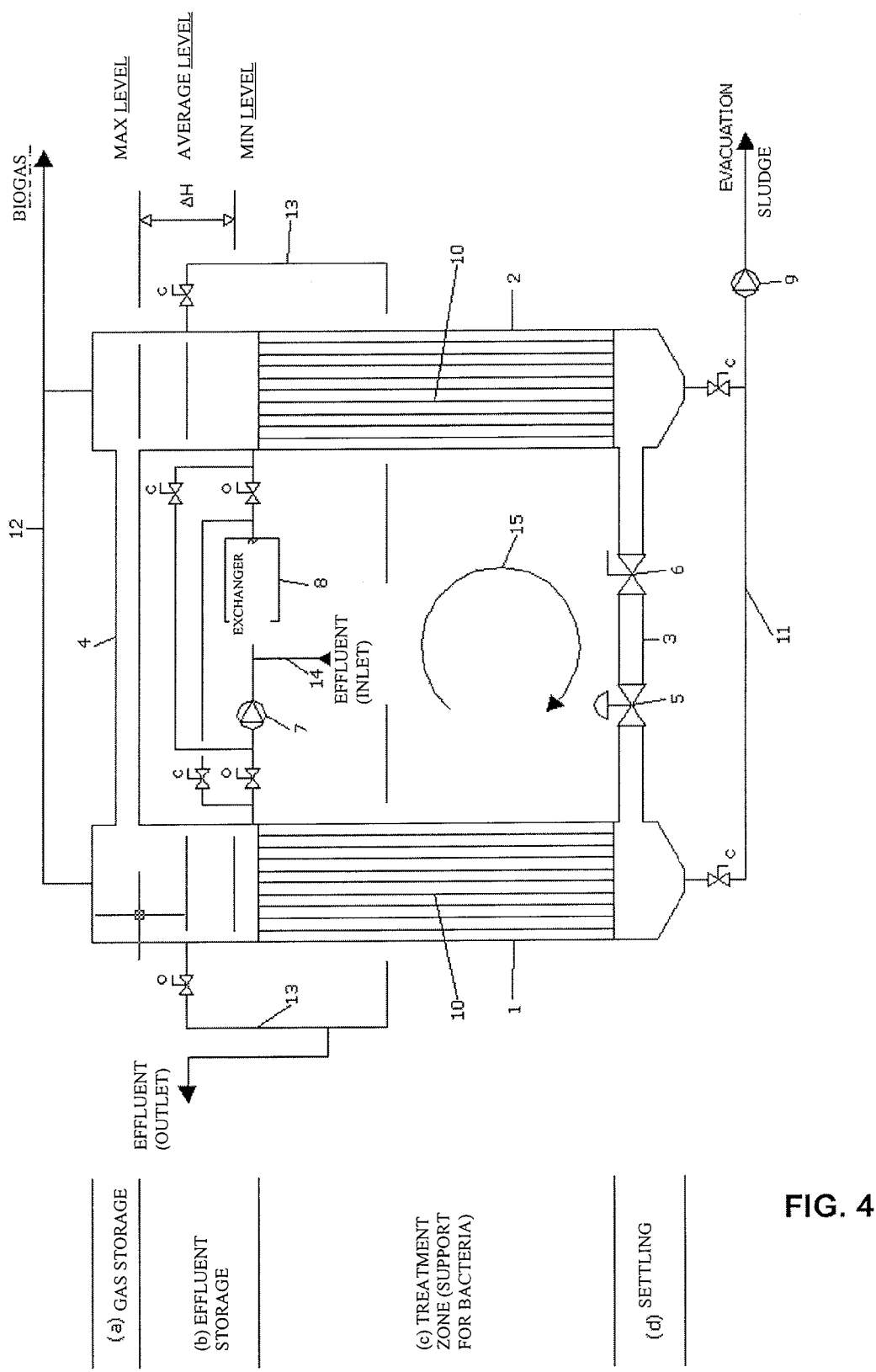

FIG. 4 is the representation of a specific case used for biomethanation.

DESCRIPTION OF THE INVENTION

The subject of this invention is an apparatus with supports for the attachment of bacteria. This apparatus helps maintain an optimum environment for bacteria growth and controlled development. This apparatus constitutes a closed environment for (liquid) effluent treatment containing substances that are digested by bacteria. The use of this apparatus in the case of biomethanation allows treating effluent loaded with putrescible organic materials in order to purify the effluent and produce biogas. At the outlet of this apparatus we obtain biogas, a purified effluent and bacteria sludge.

This digester consists of at least two tanks, similar or not, pumps, valves, heat exchanger if necessary and various measurement systems. The tanks are joined to each other by the top and bottom. A valve opens or closes the connection at the bottom of the tanks. At least one of the tanks is made up of four areas represented in the figures.

The principle of operation, excluding the start-up phase, is to periodically isolate the tanks 1, 2, from the bottom, through the isolation valve 5, to create a level difference by the recirculation pump 7 and then open the valve 5 until obtaining the equilibrium in liquid levels. This principle periodically creates strong hydrodynamic constraints and high speed of the effluent, for example until 0.25 m/s, 1 m/s, 5 m/s or even up to 10 m/s during washing. This system is different from other processes with several tanks or one tank with compartments by the use of the washing effluent storage area (b) as a reservoir for the washing of the biofilm.

The tanks are divided into four zones on the height of the tank 1, 2. A storage area of the gas produced (a) useful in the case of biomethanation, a washing effluent storage area (b), a treatment area of the effluent (c), i.e. an area where the support for the bacteria is located, and a sludge settling area (d). All known processes require at least two of these areas: the area of gas storage and the effluent treatment area. Most of the processes also have an area of sludge settling. The particularity of this invention is the use of the effluent storage area above the treatment area.

Description of the Four Areas:

a) Storage Area:

This area is used to store the gas produced before it is sent through a conduit 12 to a gas purification system if needed and then to a more substantial storage or directly used to power an engine or boiler or other apparatus running on gas. This applies to the case of biomethanation. The storage areas (a) of the various tanks 1, 2 are interconnected between them by a connecting conduit 4 to ensure pressure equalization.

b) Washing Effluent Storage Area:

This area is used to gradually store the effluent to be treated in one or more tanks, by gradually emptying one or more other tanks. For this purpose, the isolation valve 5 at the bottom of the tanks is in closed position. Therefore it creates a level difference between the different tanks 1, 2. It is this level difference that, at the opening of the isolation valve 5 at the bottom, will cause severe hydrodynamic constraints tending to equalize the levels between tanks 1, 2. Thanks to this new feature, the apparatus allows modulating the recirculation speed between 0.1 m/s and 10 m/s, for example between 1 m/s and 7 m/s, or between 2.5 m/s and 5 m/s and the frequency of recirculation which is no longer only done continuously but can also be done by batch, or a combination of two modes: for example, continuous for x minutes and then by batch, then again continuously, and preferably every one to five minutes in the case of biomethanation.

The importance of the maximum possible recirculation speed is what fundamentally differentiates this invention from other digester processes with support and recirculation. This operating mode allows for a great regulation step and can adapt to the different life stages of a digester: start-up, growth of the biofilm up to its nominal value, normal operation.

The flow of the recirculating pump 7, the frequency of the opening the isolation valve 5 and the flow control valve 6 can adapt to all types of bacteria and hence all processes of digestion by microorganisms. In biomethanation, recirculation speed is preferably between half and twice the volume of the two tanks per hour. For example, for two identical tanks with a volume of 5 m$^3$ each, the recirculation speed will range between 5 m$^3$/h and 20 m$^3$/h.

Valves allow reversing the cycle between the different tanks, which reverses the direction of the recirculation of the effluent. This reversal supports the phenomenon of detachment of the biofilm and thus facilitates the control of the thickness of the biofilm.

c) Treatment Area:

This area contains the support 10 for the attachment of bacteria, so it is mainly in this area that the effluent will be treated by digestion. The support can be either fixed or mobile.

In either case, the main characteristic of the support is to provide the maximum surface available for attachment per m$^3$.

Mobile supports can be either plastic (PVC or otherwise) or minerals, ranging in size from a few millimeters to several centimeters. Generally they come in the form of hollow balls with a maximum [number] of fins offering a large available surface.

Fixed supports are either oriented or unoriented. They can be made of plastics (PVC or otherwise) or minerals or wood. The system preferably uses vertically oriented plastic supports.

d) Settling Area:

This area allows unattached bacteria, which are in the form of sludge, to settle before being evacuated through an evacuation conduit 11 to a tank where they will be processed. This area is emptied periodically by a pump 9.

Some advantages of the process over other processes include:

The strong hydrodynamic constraints improve the accessibility of the substrate (effluent) to bacteria and thus increase the treatment capacity of the digester. In a preferred embodiment of the invention this apparatus and process can increase the processing capacity of the digester by more than 20%, and preferably more than 30%, 40%, up to more than 50%, compared to a digester of the prior art.

These constraints allow controlling the thickness of the biofilm. Preferably the thickness of a biofilm varies between 0.5 and 2 mm in the case of biomethanation.

These constraints promote degassing.

The fact that these constraints are periodic and thus the recirculation speed is discontinuous promotes the phenomenon of settling and allows for better management of sludge.

These advantages give this invention a significant advantage compared to previous inventions on the subject which give solutions for unclogging but nothing for degassing and accessibility of substrate to bacteria.

Example

Description of the Diagram (FIG. 4)

The numbering used in FIGS. 1 to 4 corresponds to the following elements:
(a) Gas storage area
(b) Effluent storage area
(c) Treatment area
(d) Settling Area
(1) tank No. 1
(2) tank No. 2
(3) connection or link conduit of the tanks from the bottom
(4) connection or link conduit of the tanks from the top
(5) isolation valve of the tanks
(6) flow control valve
(7) recirculation pump
(8) exchanger
(9) sludge evacuation pump
(10) support for the attachment of bacteria
(11) Conduit or link for sludge evacuation
(12) Conduit or link for biogas evacuation
(13) Conduit or link for effluent evacuation. This conduit is the overflow of the tanks, and it is through this conduct that the effluent comes out of the tanks after cleaning.
(14) Conduit or link for effluent: This conduit is the feeding conduit of the tanks with fresh effluent (not yet cleaned). This effluent will be cleaned in the tanks before coming out clean through conduit 13.
(15) direction of the flow or recirculation of the liquid in the tanks FIG. 4 shows a basic installation, other configurations are possible while keeping the same principle of isolation from the bottom and producing unbalanced levels in the tanks via a recirculating pump and then washing by opening one or several isolation valves.

The first tank 1 contains the four specific areas of the FAD. It is thermally isolated, if the temperature must be maintained at a certain value. Its total volume depends on the quantity of effluent to be treated and the percentage of cleaning desired.

The second tank 2 may be similar to the first or not, other tanks may be connected to the first and/or the second.

The connection conduit of the tank from the bottom 3 has a diameter sufficient to allow for optimum recirculation speed at the opening of the isolation valve. Preferably, the recirculation speed is between 100 mm/s and 1 m/sec, for example for biomethanation.

The connection conduit of the tanks from the top 4 has a diameter sufficient to allow for optimum equilibrium of gas pressure when the levels of the tanks 1, 2 vary; it also serves as overflow from one tank to another.

The isolation valve 5 allows isolating the tanks to obtain level unbalance. It is the isolation valve 5 which, by opening, will create the hydrodynamic constraints. It is an ON/OFF or proportional valve.

The flow control valve 6 allows adjusting the flow and therefore the recirculation speed.

The recirculation pump 7 allows for the recirculation of liquid from one tank to another, and also creates a level imbalance between the tanks 1, 2.

The exchangers 8 allow maintaining the liquid at a given temperature.

The evacuation pump 9 of the sludge allows draining the tanks 1, 2 periodically and evacuating the settled sludge through an evacuation conduit 11.

The support 10 for the attachment of bacteria can be fixed or mobile. If it is fixed, it can be oriented or not, made of plastic or wood. If it is mobile, it can be either BioBall type or ball or micro-ball type, made of plastic or sand or other particles type. The support must present the maximum attachment surface in $m^2/m^3$. The fixed oriented support made of PVC plastic with 200 $m^2/m^3$ ratios or more are particularly well suited to the FAD system for biomethanation.

As shown in FIG. 4, the level of effluent in the effluent storage area can vary between a maximum (Hmax) and minimum (Hmin) level. The average level (averageH) is located between the maximum (Hmax) and minimum (Hmin) levels. The average level (averageH) is the level of the liquid when the isolation valve 5 is opened, and the system has reached equilibrium levels. The maximum level (Hmax) is the maximum level which the effluent may reach when the isolation valve 5 is closed, and the recirculation pump 7 creates a hydraulic imbalance between the tanks 1, 2. The minimum level (Hmin) is the minimum level at which the effluent may reach when the isolation valve 5 is closed, and the recirculation pump 7 creates a hydraulic imbalance between the tanks 1, 2. When the tanks 1, 2 are identical, the level between Hmax and averageH is identical to the level difference between averageH and Hmin.

What is claimed is:

1. Effluent treating apparatus comprising at least two tanks joined to each other at the top and/or bottom by one or more connections in which a connection is provided between the gas storage areas of said tanks, wherein at least one of said tanks comprises
    a gas storage area (a),
    a treatment area (c) of the effluent containing a fixed or mobile support for the attachment of bacteria,
    a storage area of an effluent (b), and
    a settling area (d),
the apparatus being characterized in that
    a connection is provided between the settling areas of said tanks, said connection being provided with an isolation valve and/or a regulating valve; and
    the apparatus comprises a recirculation pump, said pump being provided on a conduit that functionally connects said tanks.

2. Apparatus according to claim 1, characterized in that the apparatus comprises valves that allow reversing the direction of the recirculation of the effluent.

3. Apparatus according to claim 1, characterized in that the gas storage area (a) is located above the area of effluent treatment (c).

4. Apparatus according to claim 1, characterized in that it comprises a conduit for the evacuation of sludge said conduit being functionally linked to the bottom of said tanks and a conduit for gas evacuation of the apparatus, said conduit eing functionally linked to the top of said tanks.

5. Apparatus according to claim 1, characterized in that the apparatus comprises an evacuation pump and/or at least one heat exchanger.

6. Washing process of an apparatus for treating an effluent according to claim 1, comprising the periodic creation of hydrodynamic constraints according to the following steps:
closing the connection of the tanks from the bottom, by closing an isolation valve of the tanks, said valve being provided on the connection linking the tanks from the bottom, in order to close the connection between tanks from the bottom, thus obtaining a volume of effluent in the effluent storage area (b) of said device,
creating a difference in the level of effluent in said tanks by activating a recirculation pump, said pump being provided on a conduit that functionally links said tanks, and
releasing in a few seconds said volume of effluent by opening the isolation volume of the tanks, until reaching the equilibrium of the effluent levels in said tanks.

7. Process according to claim 6 comprising the following steps:
obtaining a maximum volume of effluent ($H_{max}$) in the effluent storage area of one of the tanks of said apparatus, and a minimum effluent volume ($H_{min}$) in the effluent storage area of the other tank of said apparatus by closing said isolation valve of the tanks, said valve being provided on the connection linking the tanks from the bottom in order to close the connection between said tanks from the bottom,
getting a maximum difference in effluent level ($\Delta H$) in said tanks by activating a recirculation pump,
recirculating the effluent by opening the isolation valve of the tanks until obtaining an equilibrium of the level of effluent (averageH) in said tanks.

8. Process according to claim 6, in which the direction of the recirculation of the effluent can be reversed.

9. Process according to claim 6, in which the washing process is repeated periodically.

10. Process according to claim 6, comprising the determination of the speed of the effluent in the tanks by said level difference, by the passage section in the isolation valve and by the opening speed of said isolation valve.

11. Process according to claim 6, in which the recirculation speed of the effluent during the washing period ranges between 0.1 m/s and 10 m/s.

12. Process according to claim 6, in which the recirculation flow of the effluent ranges between half and twice the volume of the two tanks per hour.

13. Process according to claim 7, including the step of creating variations in effluent level, which are smaller than the maximum effluent level difference ($\Delta H$) by opening said isolation valve.

14. Process of treating effluent using an apparatus according to claim 1.

15. Process according to claim 7, in which the washing process is repeated periodically.

16. Process according to claim 7, in which the recirculation speed of the effluent during the washing period ranges between 0.1 m/s and 10 m/s.

17. Process according to claim 7, in which the recirculation flow of the effluent ranges between half and twice the volume of the two tanks per hour.

18. Process according to claim 13, wherein said isolation valve is opened periodically to obtain variations in effluent level which are smaller than the maximum effluent level difference ($\Delta H$).

19. Process of treating effluent according to claim 14, wherein anaerobic bacteria are treated.

20. Process of treating effluent according to claim 14, which comprises transforming liquid organic waste into gas.

* * * * *

UNITED STATES PATENT AND TRADEMARK OFFICE
CERTIFICATE OF CORRECTION

PATENT NO. : 8,440,084 B2  
APPLICATION NO. : 12/682119  
DATED : May 14, 2013  
INVENTOR(S) : Thomas et al.

Page 1 of 1

It is certified that error appears in the above-identified patent and that said Letters Patent is hereby corrected as shown below:

In the Claims

In column 9 at line 7, In Claim 4, change "eing" to --being--.

Signed and Sealed this  
Twelfth Day of November, 2013

Teresa Stanek Rea  
*Deputy Director of the United States Patent and Trademark Office*